(12) United States Patent  (10) Patent No.: US 8,754,044 B2
Liu  (45) Date of Patent: Jun. 17, 2014

(54) NEUROPROTECTION BY HEPATIC CELLS AND HEPATOCYTE SECRETORY FACTORS

(75) Inventor: Shu Q. Liu, Glencoe, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/462,965

(22) Filed: May 3, 2012

(65) Prior Publication Data

US 2013/0130982 A1  May 23, 2013

Related U.S. Application Data

(60) Provisional application No. 61/482,099, filed on May 3, 2011.

(51) Int. Cl.
*A61K 38/00* (2006.01)
*C07K 14/475* (2006.01)
*A61K 38/18* (2006.01)
*A61K 38/17* (2006.01)

(52) U.S. Cl.
CPC .......... *A61K 38/1833* (2013.01); *A61K 38/17* (2013.01); *A61K 38/00* (2013.01); *C07K 14/4753* (2013.01)
USPC .......................................... 514/17.7; 514/9.5

(58) Field of Classification Search
None
See application file for complete search history.

(56) References Cited

U.S. PATENT DOCUMENTS

| 7,259,248 | B2 | 8/2007 | Itoh et al. | |
|---|---|---|---|---|
| 7,655,627 | B2 | 2/2010 | Frye et al. | |
| 2006/0063204 | A1 | 3/2006 | Valkirs et al. | |
| 2008/0241208 | A1 | 10/2008 | Shanley et al. | |
| 2008/0255045 | A1* | 10/2008 | Cujec et al. | 514/12 |
| 2009/0074776 | A1* | 3/2009 | Itoh et al. | 424/139.1 |
| 2009/0305986 | A1 | 12/2009 | Belouski et al. | |
| 2011/0008281 | A1 | 1/2011 | Liu | |
| 2011/0015345 | A1 | 1/2011 | Pinkstaff et al. | |

FOREIGN PATENT DOCUMENTS

| WO | 0136640 | 5/2001 |
|---|---|---|
| WO | 03099300 | 12/2003 |
| WO | 2010065439 | 6/2010 |

OTHER PUBLICATIONS

Hsuchou et al 2007 "The fasting polypeptide fgf21 can enter brain from blood" peptides 28(12):2382-2386.*
Micanovic et al 2008 "Different roles of N- and C-termini in the functional activity of fgf21" J Cell Phys December 227-234.*
Lechner et al 2001 "basis for primary prevention of stroke under a social health act" j stroke cereb dis 10(4):145-149.*
Bargar "what is ischemic vascular disease?" accessed from http://www.wisegeek.com/what-is-ischemic-vascular-disease.htm on Oct. 10, 2013.*
Vaudry et al. 2002 "PACAP protects cerebellar granule neurons against oxidative stress-induced apoptosis" Eur J Neurosci 15 (9):1451-60 (abstract only).*
Kotton et al., "A novel stem-cell population in adult liver with potent hematopoietic-reconstitution activity" Blood, 2005, 106,1574-1580.

(Continued)

*Primary Examiner* — Jeffrey Stucker
*Assistant Examiner* — Adam M Weidner
(74) *Attorney, Agent, or Firm* — Casimir Jones S.C.

(57) ABSTRACT

The present invention relates to compositions and methods for neuroprotection. In particular, provided herein are compositions (e.g., hepatocyte secretory factors) for alleviating and/or protecting against neuronal damage (e.g., resulting from stroke), and methods of use thereof.

6 Claims, 5 Drawing Sheets

(56) References Cited

OTHER PUBLICATIONS

Kovalovich et al., "Interleukin-6 protects against Fas-mediated death by establishing a critical level of anti-apoptotic hepatic proteins FLIP, Bcl-2, and Bcl-xL," J Biol. Chem. 2001, 276, 26605-26613.
Kucia et al., "Cells expressing early cardiac markers reside in the bone marrow and are mobilized into the peripheral blood after myocardial infarction," Circ. Res. 2004, 95, 1191-1199.
Lagasse et al., "Purified hematopoietic stem cells can differentiate into hepatocytes in vivo," Nat Med. 2000, 6, 1229-1234.
Laugwitz et al., "Postnatal isl1+cardioblasts enter fully differentiated cardiomyocyte lineages," Nature, 2005, 433, 647-653.
Lee et al., "Intronic regulation of matrix metalloproteinase-2 revealed by in vivo transcriptional analysis in ischemia," Proc. Natl. Acad. Sci. USA, 2005, 102, 16345-16350.
Leor et al., "Ex vivo activated human macrophages improve healing, remodeling, and function of infarcted heart," Circulation, 2006, 114,suppl I,I-94-I-100.
Li, Y., et al., "Postinfarction treatment with an adenoviral vector expressing hepatocyte growth factor relieves chronic left ventricular remodeling and dysfunction in mice," Circulation, 2003, 107, 2499-2506.
Liu et al. "Liver cell-mediated alleviation of acute ischemic myocardial injury," Frontiers in Bioscience (Elite Ed), 2: 711-724, 2010A.
Liu et al., "Evidence for a role of basic fibroblast growth factor in rat embryonic growth and differentiation," Endocrinology, 1988, 123(4):2027-31.
Liu, et al., "Formation of smooth muscle σ actin filaments in CD34-positive bone marrow cells in elastic lamina-dominant matrix of arteries," Matrix Biology, 2008, 27, 282-294.
Liu, et al., "Negative regulation of monocyte adhesion to arterial elastic laminae by signal-regulatory protein alpha and SH2 domain-containing protein tyrosine phosphatase-1," J. Biol. Chem. 2005, 280, 39294-39301.
Lunde, et al., "Intracoronary injection of mononuclear bone marrow cells in acute myocardial infarction," N. Engl. J. Med. 2006, 355, 1199-1209.
Maeda et al., "Pathology of experimental radiation pancarditis. I. Observation on radiation-induced heart injuries following a single dose of x-ray irradiation to rabbit heart with special reference to its pathogenesis," Acta Pathol Jpn, 1980, 30(1):59-78.
Malin, et al., "Production of dissociated sensory neuron cultures and considerations for their use in studying neuronal function and plasticity," Nature Protocols, 2007, 2, 152-160.
Martins, et al., "Rodent models of partial hepatectomies," Liver Int, 2008, 28, 3-11.
Matsuoka, et al., "Neural crest origins of the neck and shoulder," Nature, 2005, 436, 347-355.
Michalopoulos et al. "Liver regeneration," Science, 1997, 276: 60-66.
Mohammadi et al. "A protein canyon in the FGF-FGF receptor dimer selects from an à la carte menu of heparan sulfate motifs," Curr Opin Sruct Biol, 2005, 15: 506-516.
Morimoto, et al., "Bone marrow-derived CXCR4+ cells mobilized by macrophage colony-stimulating factor participate in the reduction of infarct area and improvement of cardiac remodeling after myocardial infarction in mice," Am J Pathol. 2007, 171, 755-766.
Moser et al., "BMPER, a novel endothelial cell precursor-derived protein, antagonizes bone morphogenetic protein signaling and endothelial cell differentiation," Mol Cell Biol. 2003, 23(16):5664-79.
Murphy, G. "Matrix metalloproteinases and their inhibitors," Acta Orthop Scand Suppl, 1995,266, 55-60.
Murry, et al., "Haematopoietic stem cells do not transdifferentiate into cardiac myocytes in myocardial infarcts," Nature, 2004, 428, 664-668.
Nair et al. "Novel effector molecules in type 2 inflammation: lessons drawn from helminth infection and allergy," J Immunol, 2006, 177: 1393-1399.
Nakamura, et al., "Myocardial protection from ischemia/reperfusion injury by endogenous and exogenous HGF," J Clin Invest, 2000, 106, 1511-1519.
Nishimoto et al., "Interleukin 6: from bench to bedside," Nat Clin Pract Rheumatol, 2006, 2, 619-626.
Nishimura et al. "Identification of a novel FGF, FGF-21, preferentially expressed in the liver," Biochim Biophsy Acta, 2000, 1492: 203-206.
Nygren, et al., "Bone marrow-derived hematopoietic cells generate cardiomyocytes at a low frequency through cell fusion, but not transdifferentiation.," Nat. Med. 2004, 10, 494-501.
Orlic, et al., "Mobilized bone marrow cells repair the infarcted heart, improving function and survival," Proc Natl Acad Sci U S A , 2001, 98, 10344-10349.
Osypiw, et al., "Subpopulations of rat hepatocytes separated by Percoll density-gradient centrifugation show characteristics consistent with different acinar locations," Biochem. J. 1994, 304, 617-624.
Passier, et al., "Stem-cell-based therapy and lessons from the heart," Nature, 2008, 453, 322-329.
Postic, et al., "Dual Roles for Glucokinase in Glucose Homeostasis as Determined by Liver and Pancreatic Cell-specific Gene Knock-outs Using Cre Recombinase," J Biol Chem, 1999, 274, 305-315.
Rehman, et al., 2003, "Peripheral blood "endothelial progenitor cells" are derived from monocyte/macrophages and secrete angiogenic growth factors," Circulation, 2007, 107, 1164-1169.
Rota, et al., "Bone marrow cells adopt the cardiomyogenic fate in vivo," Proc Natl Acad Sci USA , 2007, 104, 17783-17788.
Rota, et al., "Local activation or implantation of cardiac progenitor cells rescues scarred infarcted myocardium improving cardiac function," Circ Res. 2008, 103, 107-116.
Ryden, "Fibroblast growth factor 21: an overview from a clinical perspective," Cell Mol Life Sci, 2009, 66: 2067-2073.
Sands et al. "The trefoil peptide family," Annu Rev Physiol, 1996, 58: 253-273.
Schindl, et al., "The value of residual liver volume as a predictor of hepatic dysfunction and infection after major liver resection.," Gut, 2005, 54, 289-296.
Schinke et al. "Cloning and functional characterization of resistin-like molecule gamma," Biochem Biophys Res Commun, 2004, 314: 356-362.
Schlüter, et al., "Adult ventricular cardiomyocytes: isolation and culture" Methods Mol Biol., 2005, 290, 305-314.
Segers et al., "Stem-cell therapy for cardiac disease" Nature, 2008, 451, 937-942.
Seglen, P.O. "Hepatocyte suspensions and cultures as tools in experimental carcinogenesis," J. Toxicol. Environ. Health , 1979, 5(2-3), 551-560.
Sehgal, et al., "Human chromosome 7 carries the beta-2 interferon gene," Proc Nat Acad Sci USA, 1986, 83, 5219-5222.
Shibata, et al., "Adiponectin protects against the development of systolic dysfunction following myocardial infarction,"J. Mol. Cell Cardiol. 2007, 42, 1065-1074.
Shojima et al. "Serum concentrations of resistin-like molecules beta and gamma are elevated in high-fat-fed and obese db/db mice, with increased production in the intestinal tract and bone marrow," Diabetologia, 2005, 48: 984-992.
Skinner, et al., "Transcriptional activation and transformation by FosB protein require phosphorylation of the carboxyl-terminal activation domain," Mol Cell Biol, 1997, 17, 2372-2380.
Srinivas, et al., "Cre reporter strains produced by targeted insertion of EYFP and ECFP into the ROSA26 locus," BMC Dev Biol. 2001;1:4. Epub Mar. 27, 2001.
Stadtfeld et al., "Assessing the role of hematopoietic plasticity for endothelial and hepatocyte development by non-invasive lineage tracing" Development, 2005, 132, 203-213.
Steppan et al. "The hormone resistin links obesity to diabetes," Nature, 2001, 409(6818): 307-312.
Stern et al, "Tracing the lineage of tracing cell lineages," Nat Cell Biol. 2001, 3, E216-218.
Alison et al. "Wound healing in the liver with particular reference to stem cells," Philos Trans R Lond B Biol Sci, 1998, 353: 877-894.
Almeida-Porada, et al., "Formation of human hepatocytes by human hematopoietic stem cells in sheep," Blood, 2004, 104, 2582-2590.

(56) References Cited

OTHER PUBLICATIONS

Angel et al., "The role of Jun, Fos, and AP-1 complex in cell proliferation and transformation," Biochim. Biophys. Acta. 1991,1072, 129-157.
Appenheimer, et al., "Conservation of IL-6 trans-signaling mechanisms controlling L-selectin adhesion by fever-range thermal stress," European Journal of Immunology, 2007, 37, 2856-2867.
Arita et al., "Increased islet viability by addition of beraprost sodium to collagenase solution," Pancreas, 2001, 23, 62-67.
Badman et al., "Hepatic fibroblast growth factor 21 is regulated by PPARalpha and is a key mediator of hepatic lipid metabolism in ketotic states," Cell Metab. 2007, 5(6):426-37.
Badorff, et al., "Transdifferentiation of blood-derived human adult endothelial progenitor cells into functionally active cardiomyocytes," Circulation, 2003, 107, 1024-1032.
Balsam, et al., "Haematopoietic stem cells adopt mature haematopoietic fates in ischaemic myocardium," Nature, 2004, 428, 668-673.
Beltrami et al., "Adult cardiac stem cells are multipotent and support myocardial regeneration," Cell, 2003, 2003, 114, 763-776.
Bergman, et al., "A functional activating protein 1 AP-1 site regulates matrix metalloproteinase 2 MMP-2 transcription by cardiac cells through interactions with JunB-Fra1 and JunB-FosB heterodimers," Biochem. J. 2003, 369, 485-496.
Biasucci, et al., "Elevated levels of interleukin-6 in unstable angina," Circulation, 1996, 94, 874-877.
Brunner, et al., "Erythropoietin administration after myocardial infarction in mice attenuates ischemic cardiomyopathy associated with enhanced homing of bone marrow-derived progenitor cells via the CXCR-4/SDF-1 axis," FASEB J. 2009, 23, 351-361.
Buchan et al. "A new model of temporary focal neocortical ischemia in the rat," Stroke, 1992, 23: 273-273.
Cai, et al., "Suppression of hepatocyte growth factor production impairs the ability of adipose-derived stem cells to promote ischemic tissue revascularization.," Stem Cells, 2007, 25: 3234-3243.
Carrasco et al., "Trefoil Factor Family Peptide 3 Prevents the Development and Promotes Healing of Ischemia-Reperfusion Injury in Weanling Rats," J Pediatric Surg., 2004, 39:1693-1700.
Chen, et al., "Central role of IL-6 receptor signal-transducing chain gp130 in activation of L-selectin adhesion by fever-range thermal stress," Immunity, 2004, 20, 59-70.
Chumakov et al. "Identification of murine and human XCP1 genes as C/EBP-epsilon-dependent members of FIZZ/Resistin gene family," Oncogene, 2004, 23: 3414-3425.
Cleutjens, et al., "Collagen remodeling after myocardial infarction in the rat heart," Am J Path, 1995, 147, 325-338.
Cressman, et al., "Liver failure and defective hepatocyte regeneration in interleukin-6-deficient mice," Science, 1996, 274, 1379-1383.
Dill, et al., "Intracoronary administration of bone marrow-derived progenitor cells improves left ventricular function in patients at risk for adverse remodeling after acute ST-segment elevation myocardial infarction: results of the Reinfusion of Enriched Progenitor cells and Infarct Remodeling in Acute Myocardial Infarction study REPAIR-AMI cardiac magnetic resonance imaging substudy," Am Heart J, 2009, 157, 541-547.
Dostalova et al. "Fibroblast growth factor 21: a novel metabolic regulator with potential therapeutic properties in obesity/type 2 diabetes mellitus," Physiol Res, 2009, 58: 1-7.
Eerola, et al., "The Influence of Percutaneous Closure of Patent Ductus Arteriosus on Left Ventricular Size and Function—A Prospective Study Using Two- and Three-Dimensional Echocardiography and Measurements of Serum Natriuretic Peptides," J. Am. Coll. Cardiol. 2006, 47, 1060-1066.
Fausto et al. "The role of hepatocytes and oval cells in liver regeneration and repopulation," Mech Dev, 2003, 120: 117-130.
Fazel, et al., "Activation of c-kit is necessary for mobilization of reparative bone marrow progenitor cells in response to cardiac injury," FASEB J. 2008, 22, 930-940.

Fisman, et al., "Interleukin-6 and the risk of future cardiovascular events in patients with angina pectoris and/or healed myocardial infarction.," Am J Cardiol. 2006, 98, 14-18.
Forbes, et al., "Hepatic stem cells," J Pathol. 2002, 197, 510-518.
Fournier et al., "Alpha-1-acid glycoprotein," Biochim Biophys Acta. 2000,1482(1-2):157-71.
Fukumoto et al., "Actions and mode of actions of FGF19 subfamily members," Endocr J. 2008, 55(1):23-31.
Gerstmayer et al. "Identification of RELMgamma, a novel resistin-like molecule with a distinct expression pattern," Genomics,2003, 81: 588-595.
Greene et al., "Partial hepatectomy in the mouse: technique and perioperative management," J Invest Surg, 2003, 16, 99-102.
Guerre-Millo et al., "Peroxisome proliferator-activated receptor alpha activators improve insulin sensitivity and reduce adiposity," J Biol Chem. 2000, 275(22):16638-16642.
Gyöngyösi, et al., "Combined delivery approach of bone marrow mononuclear stem cells early and late after myocardial infarction: the MYSTAR prospective, randomized study," Nat Clin Pract Cardiovasc Med, 2009, 6, 70-81.
Harari et al., "Neuregulin-4: a novel growth factor that acts through the ErbB-4 receptor tyrosine kinase," Oncogene. 1999, (17):2681-9.
Hayes et al., "Characterization of the cell membrane-associated products of the Neuregulin 4 gene," Oncogene. 2008, 27(5):715-20.
Heinke et al., "BMPER is an endothelial cell regulator and controls bone morphogenetic protein-4-dependent angiogenesis," Circ Res. 2008, 103(8):804-12.
Hirano, et al., "Complementary DNA for a novel human interleukin BSF-2 that induces B lymphocytes to produce immunoglobulin," Nature, 1986, 324, 73-76.
Hofmann, et al. "Matrix metalloproteinases in human melanoma," J Invest Dermatol. 2000, 115, 337-344.
Hotta et al., "Fibroblast growth factor 21 regulates lipolysis in white adipose tissue but is not required for ketogenesis and triglyceride clearance in liver," Endocrinology. 2009, 150(10):4625-33.
Huotari et al., "ErbB signaling regulates lineage determination of developing pancreatic islet cells in embryonic organ culture," Endocrinology. 2002, 143(11):4437-46.
Ibrahimi et al. "Kinetic model for FGF, FGFR, and proteoglycan signal transduction complex assembly," Biochemistry, 2004, 43: 4724-4730.
II, M. et al., "Endothelial progenitor cells are rapidly recruited to myocardium and mediate protective effect of ischemic preconditioning via "imported" nitric oxide synthase activity," Circulation, 2005, 111, 1114-1120.
Ikeya et al., "Essential pro-Bmp roles of crossveinless 2 in mouse organogenesis," Development. 2006, 133 (22):4463-73.
Inagaki et al., "Endocrine regulation of the fasting response by PPARalpha-mediated induction of fibroblast growth factor 21," Cell Metab. 2007, 5(6):415-25.
Itoh et al. "Evolution of the Fgf and Fgfr gene families," Trends Genet, 2004, 20: 563-569.
Iwakura, et al., "Estradiol enhances recovery after myocardial infarction by augmenting incorporation of bone marrow-derived endothelial progenitor cells into sites of ischemia-induced neovascularization via endothelial nitric oxide synthase-mediated activation of matrix metalloproteinase-9," Circulation, 2006, 113, 1605-1614.
Johns, et al., "Isolation of renin-rich rat kidney cells," Hypertension, 1987, 10, 488-496.
Jurasz, et al., "Matrix Metalloproteinase 2 in Tumor Cell-induced Platelet Aggregation: Regulation by Nitric Oxide," Cancer Research, 2001, 61, 376-382.
Kharitonenkov et al. "FGF-21 as a novel metabolic regulator," J Clin Invest, 2005, 115: 1627-1635.
Kopf, et al., "Impaired immune and acute-phase responses in interleukin-6-deficient mice," Nature, 1994, 368, 339-342.
Kossakowska, et al., "Interleukin-6 regulation of matrix metalloproteinase MMP-2 and MMP-9 and tissue inhibitor of metalloproteinase TIMP-1 expression in malignant non-Hodgkin's lymphomas," Blood, 1999, 94, 2080-2089.

(56) References Cited

OTHER PUBLICATIONS

Taga et al., "Gp130 and the interleukin-6 family of cytokines," Annu Rev Immunol. 1997, 15, 797-819.

Taniyama, et al., "Potential contribution of a novel antifibrotic factor, hepatocyte growth factor, to prevention of myocardial fibrosis by angiotensin II blockade in cardiomyopathic hamsters," Circulation, 2000, 102, 246-252.

Taub, "Liver regeneration: from myth to mechanism," Nat Rev Mol Cell Biol, 2004, 5: 836-847.

Urbanek, et al., "Cardiac stem cells possess growth factor-receptor systems that after activation regenerate the infarcted myocardium, improving ventricular function and long-term survival," Circ. Res. 2005, 97, 663-673.

Vallette et al. "Construction of mutant and chimeric genes using the polymerase chain reaction," Nucl Acis Res, 1989, 17: 723-733.

Van Molle et al., "Activation of caspases in lethal experimental hepatitis and prevention by acute phase proteins," J Immunol. 1999, 163(10):5235-41.

Van Molle et al., "Alpha 1-acid glycoprotein and alpha 1-antitrypsin inhibit TNF-induced but not anti-Fas-induced apoptosis of hepatocytes in mice," J Immunol. 1997, 159(7):3555-64.

Vremec, et al., "The surface phenotype of dendritic cells purified from mouse thymus and spleen: investigation of the CD8 expression by a subpopulation of dendritic cells," J Exp Med. 1992, 176, 47-58.

Westermark et al. "Serum amyloid A and protein AA: molecular mechanisms of a transmissible amyloidosis," FEBS Letters, 2009, 583: 2685-2690.

Wong et al. "Trefoil peptides," Gut, 1999, 44: 890-895.

Zar, J.H. Biostatistical Analysis. 2nd Ed., 1984. Prentice Hall, Englewood Cliffs, New Jersey.

Zhang et al. "Receptor specificity of the fibroblast growth factor family. The complete mammalian FGF family," J Biol Chem, 2006, 281: 15694-15700.

Zou, et al., "Leukemia inhibitory factor enhances survival of cardiomyocytes and induces regeneration of myocardium after myocardial infarction," Circulation, 2003, 108, 748-753.

International Search Report and Written Opinion for PCT/US2012/036232, mailed Jul. 26, 2012, 12 pages.

* cited by examiner

NEUROPROTECTION BY HEPATIC CELLS AND HEPATOCYTE SECRETORY FACTORS

CROSS-REFERENCE TO RELATED APPLICATIONS

The present invention claims the benefit of U.S. Provisional Patent Application Ser. No. 61/482,099, filed May 3, 2011, which is incorporated by reference in its entirety.

STATEMENT REGARDING FEDERAL FUNDING

This invention was made with government support under Grant Number CBET0932131 awarded by the National Science Foundation. The government has certain rights in the invention.

FIELD OF THE INVENTION

The present invention relates to compositions and methods for neuroprotection. In particular, provided herein are compositions (e.g., hepatocyte secretory factors) for alleviating and/or protecting against neuronal damage (e.g., resulting from stroke), and methods of use thereof.

BACKGROUND

Cerebral ischemia or ischemic stroke induces neuronal injury and death. As adult neurons possess a limited capacity of protection against ischemic injury, infarcted brain is often replaced with fibrotic tissues, resulting in permanent impairment of nervous functions. One desired therapeutic approach is to protect the brain from ischemic injury during the acute phase of stroke, minimizing the loss of neurons. However, few effective therapies have been established for such a purpose in prior research.

SUMMARY OF THE INVENTION

The present invention provides methods, compositions, and systems for treating a subject experiencing, at risk for, with, suffering from, or suspected of having cerebral ischemia using hepatocyte secretory factors (e.g., FGF21, RELMγ, TFF3). In some embodiments, the present invention provides administering hepatocyte secretory factors to a subject to treat cerebral ischemia. In some embodiments, the present invention provides administering hepatocyte secretory factors whose serum concentration is increased in response to cerebral ischemia. In some embodiments, administration of hepatocyte secretory factors reduces ischemic injury in the subject. In some embodiments, administration of hepatocyte secretory factors exerts a neuroprotective effect. In some embodiments, administration of hepatocyte secretory factors results in reduction in cerebral infarction. In some embodiments, compositions are administered before, during, and/or after a stroke or other cause of cerebral infarction or other neuronal injury.

In some embodiments, the present invention provides methods of treating a subject experiencing cerebral ischemia, the effects of cerebral ischemia, or conditions similar to cerebral ischemia comprising: administering a composition to the subject, wherein the composition comprises at least one isolated hepatocyte secretory factor. In some embodiments, the serum concentration of the secretory factor is increased in response to cerebral ischemia (e.g., FGF21, RELMγ, TFF3). In certain embodiments, the administration reduces cerebral injury in the subject. In some embodiments, administration of secretory factors (e.g., FGF21, RELMγ, TFF3) exerts a neuroprotective effect. In some embodiments, secretory factors are administered in a combination that exerts a neuroprotective effect, results in reduction in cerebral infarction, and/or reduces ischemic injury. In some embodiments, the at least one isolated hepatocyte secretory factor is selected from the group consisting of: hepatocyte secreted proteins including fibroblast growth factor 21 (FGF21) or a biologically active fragment or variant thereof, resistin like molecule γ (RELMγ) or a biologically active fragment or variant thereof, and trefoil factor 3 (TFF3) or a biologically active fragment or variant thereof.

In certain embodiments, the at least one isolated hepatocyte secretory factor is administered at a dosage of 1 μg/kg-500 mg/kg (e.g., 1 μg/kg . . . 5 μg/kg . . . 10 μg/kg . . . 20 μg/kg . . . 50 μg/kg . . . 100 μg/kg . . . 200 μg/kg . . . 500 μg/kg . . . 1 mg/kg . . . 2 mg/kg . . . 5 mg/kg . . . 10 mg/kg . . . 20 mg/kg . . . 50 mg/kg . . . 100 mg/kg . . . 200 mg/kg . . . 500 mg/kg). In certain embodiments, the at least one isolated hepatocyte secretory factor is administered at a dosage of about 1.0 mg to 1000 mg (e.g., 1.0 mg . . . 2.0 mg . . . 5.0 mg . . . 10 mg . . . 20 mg . . . 50 mg . . . 100 mg . . . 200 mg . . . 500 mg . . . 1000 mg). In some embodiments, the at least one isolated hepatocyte secretory factor comprises two, three, four, five, or more isolated hepatocyte secretory factors.

In some embodiments, the subject is a human and the at least one isolated hepatocyte secretory factor is a human hepatocyte secretory factor or active fragment or variant thereof. The at least one isolated hepatocyte secretory factor can be administered intravenously, orally, transdermally, surgically (e.g., direct administration to the brain), or by any other suitable route of administration.

In certain embodiments, the subject is someone without cerebral ischemic tissue injury, but is at risk for such injury (e.g., the composition is administered prophylacticly to prevent anticipated ischemic injury). In some embodiments, the subject is experiencing a stroke. In some embodiments, the subject had a stroke in the recent past.

In some embodiments, compositions comprising hepatocyte secretory factors (e.g., FGF21, RELMγ, TFF3) are administered with other therapeutic composition to exert a neuroprotective effect and/or treat, prevent, alleviate cerebral infarction.

In particular embodiments, the subject is a mammal. In other embodiments, the subject is a human. In some embodiments, the subject is diagnosed as having cerebral ischemia. In some embodiments, the subject is suspected of having cerebral ischemia. In some embodiments, the subject is at risk of having cerebral ischemia.

In some embodiments, the present invention provides a composition comprising one or more isolated hepatocyte secretory factors configured for pharmaceutical administration to a subject experiencing cerebral ischemia. In some embodiments, the one or more isolated hepatocyte secretory factors are selected from the group comprising: FGF21 or a biologically active fragment or variant thereof, RELMγ or a biologically active fragment or variant thereof, and TFF3 or a biologically active fragment or variant thereof. In some embodiments, pharmaceutical administration is by oral, parenateral, topical, intravenous, transmucosal, surgical, and/or inhalation routes. In some embodiments, a composition further comprises a physiologically tolerable buffer. In certain embodiments, the present invention provides small molecules that cause an increase in one or more of the above isolated hepatocyte secretory factors.

In some embodiments, the present invention provides methods of preventing cerebral ischemia in a subject at risk for experiencing cerebral ischemia comprising: administering a composition to said subject, wherein said composition comprises at least one isolated hepatocyte secretory factor whose serum concentration is increased in response to cerebral ischemia. In other embodiments, at least one isolated hepatocyte secretory factor whose serum concentration is increased in response to cerebral ischemia is selected from the group comprising: FGF21 or a biologically active fragment or variant thereof, RELMγ or a biologically active fragment or variant thereof, and TFF3 or a biologically active fragment or variant thereof. In other embodiments, the administration of said composition exerts a neuroprotective effect.

DETAILED DESCRIPTION

Figure 1:
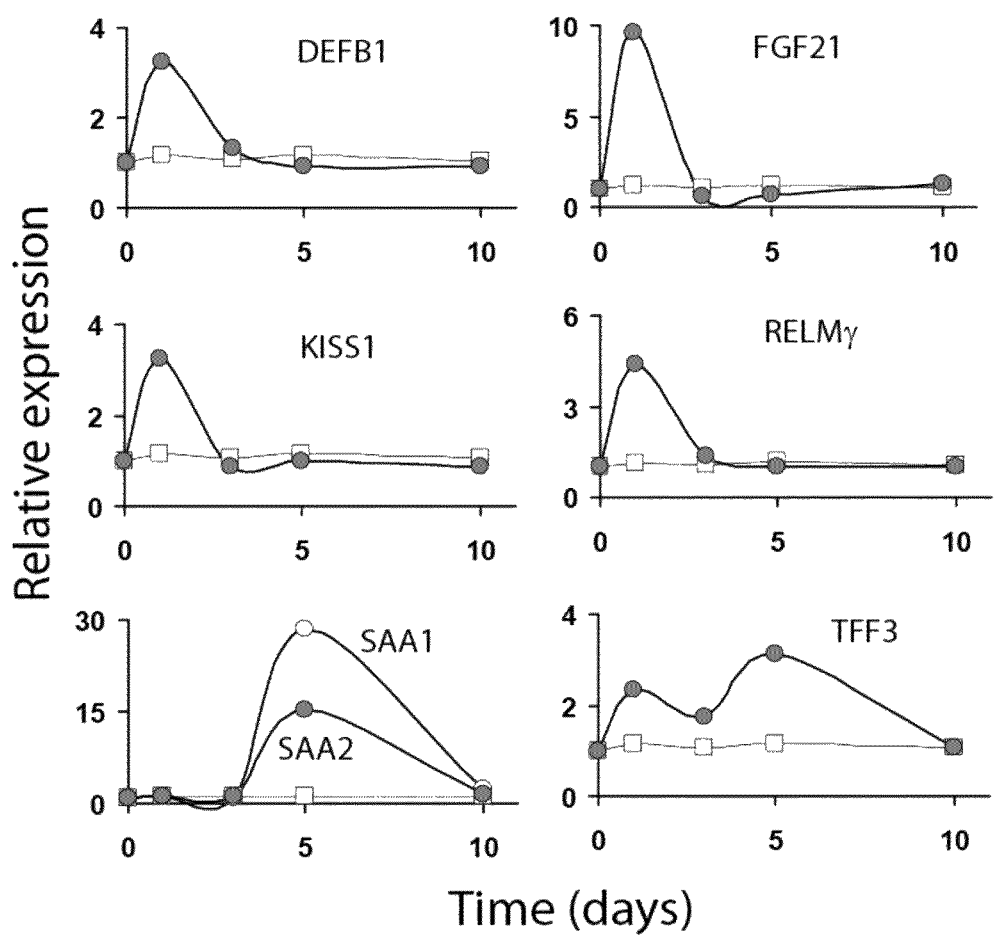
FIG. 1 shows relative levels of mRNA transcription from genes encoding hepatocyte secreted proteins DEFB1, FGF21, KISS1, RELMγ, SAA1, SAA2, and TFF3 in hepatocytes in cerebral ischemia. For each gene, the time zero represents the sham control level. The "relative expression" was defined as the ratio of the mRNA transcription level at a given time to the sham control level. The open squares in each panel represent the relative expression of the β actin gene.

Adult neurons possess a limited capacity of protection against ischemic injury. In the event of cerebral ischemia, non-neuronal cells are often involved in neuroprotection, contributing to minimization of neuronal injury and death. Experiments conducted during development of embodiments of the present invention demonstrated that hepatocytes were activated in response to cerebral ischemia to contribute to neuroprotection. These cells upregulate genes encoding secreted proteins including defensin beta 1 (DEFB1), fibroblast growth factor 21 (FGF21), kisspeptin 1 (KISS1), resistin like molecule γ (RELMγ), and trefoil factor 3 (TFF3) in cerebral ischemia. Functional screening tests identified three secreted proteins, including FGF21, RELMγ, and TFF3, that exerted a neuroprotective effect. Administration of mouse recombinant FGF21, RELMγ, or TFF3 to mice with cerebral ischemia resulted in a significant reduction in cerebral infarction and improvement of the gripping strength of the impaired forelimb. These observations indicate that the secreted factors FGF21, RELMγ, and TFF3 upregulated in hepatocytes in response to stroke provide utility in alleviating brain ischemic injury.

Depending on species, FGF21 is generally a 208-210 amino acid protein belonging to the FGF family that includes 22 members. This protein is primarily expressed in the liver and, to a lesser degree, in the thymus and adipose tissue (Nishimura et al., 2000; Ryde'n 2009; herein incorporated by reference in their entireties). The amino acid sequence (SEQ ID NO:1) and the nucleic acid sequence (SEQ ID NO:2) of human FGF21 are shown in the sequence listing. While the majority of FGF members play a role in regulating cell proliferation and differentiation, FGF21 together with FGF 19 has been reported to regulate glucose and lipid metabolisms (Itoh and Ornitz, 2004; Dostálová et al., 2009; herein incorporated by reference in their entireties). FGF21 mediates these metabolic activities via interacting with FGF Receptor 2α, resulting in activation of the ERK1/2 and Akt signaling pathways (Ibrahimi et al., 2004; Kharitonenkov et al., 2005; Mohammadi et al., 2005; Zhang et al., 2006; herein incorporated by reference in their entireties). These signaling pathways may be responsible for FGF21-induced cell activities; although, the present invention is not limited to any particular mechanism of action and an understanding of the mechanism of action is not necessary to practice the present invention.

RELMγ, also known as resistin like γ (Retnlg), is a secreted cysteine-rich protein (117 amino acids, ~7 kDa) belonging to the RELM family, which is composed of RELMα and RELMβ in addition to RELMγ (Gerstmayer et al., 2003; Schinke et al., 2004; Chumakov et al., 2004; herein incorporated by reference in their entireties). These molecules display considerable sequence homology to resistin, a secreted protein that negatively regulates the sensitivity of cells to insulin (Steppan et al., 2001; Nair et al., 2006; herein incorporated by reference in their entireties). RELMγ is primarily expressed in the lung, spleen, pancreas, small and large intestines, and bone marrow (Shojima et al., 2005; Gerstmayer et al., 2003; Schinke et al., 2004; Chumakov et al., 2004; herein incorporated by reference in their entireties). This molecule may form homodimers and heterodimers with RELMβ, and has been reported to stimulate the proliferation and differentiation of promyelocytic cells in the rat (Schinke et al., 2004; herein incorporated by reference in its entirety), and suspected to mediate inflammatory responses and cause insulin resistance (Nair et al., 2006; Shojima et al., 2005; herein incorporated by reference in their entireties). RELMγ receptors and associated signaling pathways have not been identified. It is important to note that, under physiological conditions, RELMγ is not expressed in the liver. Experiments conducted during development of embodiments of the present invention demonstrated that hepatocyte mRNA transcription for the RELMγ gene was upregulated for 4.4 times in cerebral ischemia compared to the sham control. These observations indicate that RELMγ is upregulated in response to cerebral ischemia, although the signaling mechanisms remain to be addressed. In some embodiments of the present invention, RELMβ is administered to a subject in place or, or in conjunction with RELMγ.

TFF3 is a protein expressed primarily in mucus-secreting goblet cells of the gastrointestinal tract (Sands and Podolsky 1996; herein incorporated by reference in its entirety). The amino acid sequence (SEQ ID NO:5) and the nucleic acid sequence (SEQ ID NO:6) of human TFF3 are shown in the sequence listing. TFF 3 has been shown to contribute to the maintenance of the mucosal integrity and facilitate mucosal healing and repair after mechanical and chemical injury (Sands and Podolsky 1996; Wong et al., 1999; herein incorporated by reference in their entireties).

Experiments conducted during development of embodiments of the present invention demonstrated the contribution of these factors to neuroprotection against ischemic injury.

The hepatocyte secretory factors may be administered in combinations of two of more factors (e.g., as a single combination or sequentially administered). Exemplary combinations of factors, which can consist of or comprise these combinations, are shown in Table 1 below:

TABLE 1

| Combination 1 | FGF21 | | |
|---|---|---|---|
| Combination 2 | FGF21 | RELMγ | |
| Combination 3 | FGF21 | TFF3 | |
| Combination 4 | TFF3 | RELMγ | |
| Combination 5 | FGF21 | RELMγ | TFF3 |
| Combination 5 | RELMγ | | |
| Combination 5 | TFF3 | | |

In some embodiments, the combinations listed in Table 1 are combined with one or more additional hepatocyte secretory factors for administration to a subject. In some embodiments, the combinations listed in Table 1 are combined with one or more additional therapeutic agents for administration to a subject.

In certain embodiments, the present invention provides a sequence variant of a hepatocyte secretory factor, such as FGF21, RELMγ, and/or TFF3, including, for example, a deletion, insertion, mutation, or the like, that is useful in treating, preventing, or alleviating cerebral ischemic injury. Such a sequence variant or fragment is termed a "biologically active fragment or variant" of a hepatocyte secretory factor. In some embodiments, a biologically active fragment or variant provides one or more portions of a hepatocyte secretory factor, such as FGF21, RELMγ, and/or TFF3. In some embodiments, a biologically active portions or fragments of a hepatocyte secretory factor, such as FGF21, RELMγ, and/or TFF3 is useful in treating, preventing, or alleviating cerebral ischemic injury. In some embodiments, biologically active fragment or variant of a hepatocyte secretory factor includes, polypeptides having at least 70% identity to FGF21, RELMγ, and/or TFF3 (e.g., have a sequence identity to FGF21, RELMγ, and/or TFF3 that is >99% . . . >98% . . . >95% . . . >90% . . . >85% . . . >80% . . . >75% . . . >70%). A biologically active fragment or variant of a hepatocyte secretory factor can include a polypeptide that has at least 20 amino acids having at least 70% identity to a contiguous portion of FGF21, RELMγ, or TFF3. For example, a biologically active fragment or variant of a hepatocyte secretory factor includes a polypeptide comprising a hepatocyte secretory factor, such as FGF21, RELMγ, and/or TFF3 with an N-terminal deletion of up to 100 amino acids. In another example, a biologically active fragment or variant of a hepatocyte secretory factor includes a polypeptide comprising a hepatocyte secretory factor, such as FGF21, RELMγ, and/or TFF3 with a C-terminal deletion of up to 100 amino acids. One can determine if various truncations or variants of the secretory factors function in a neuroprotective capacity by substituting in these truncations or variants in the Examples below.

In some embodiments, the present invention provides one or more conserved portions of a hepatocyte secretory factor, such as FGF21, RELMγ, and/or TFF3. The present invention also contemplates sequences that have at least 70% (e.g., 70% . . . 75% . . . 80% . . . 85% . . . 90% . . . 95%, 96%, 97%, 98%, 99%, or 99.5%) sequence identity to a hepatocyte secretory factor, such as FGF21, RELMγ, and/or TFF3 and/or exhibits substantially the same, or similar, activity (e.g., treating, preventing, or alleviating cerebral ischemic injury). For example, one or two amino acids may be changed (or one or two codons changed in the nucleic acid) such that a sequence differing by one or two amino acid residues is generated. In some embodiments, multiple amino acids in these sequences are changed (or codons in nucleic acids coding these sequences) while maintaining similar secondary structure and/or tertiary structure, and maintaining activity. Changes to the amino acid sequence may be generated by changing the nucleic acid sequence encoding the amino acid sequence.

Nucleic acid encoding a variant of a given portion of these sequences may be prepared by methods known in the art. These methods include, but are not limited to, preparation by site-directed (or oligonucleotide-mediated) mutagenesis, PCR mutagenesis, and cassette mutagenesis of an earlier prepared nucleic acid encoding a hepatocyte secretory factor, such as FGF21, RELMγ, and/or TFF3. Site-directed mutagenesis is a preferred method for preparing substitution variants. This technique is well known in the art (see, e.g., Carter et al. Nucleic Acids Res. 13: 4431-4443 (1985) and Kunkel et. al., Proc. Natl. Acad. Sci. USA 82: 488 (1987), both of which are hereby incorporated by reference).

Briefly, in carrying out site directed mutagenesis of DNA, the starting DNA is, for example, altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of a hepatocyte secretory factor, such as FGF21, RELMγ, and/or TFF3 (see, e.g., Vallette et. al., Nuc. Acids Res. 17: 723-733 (1989), hereby incorporated by reference). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34: 315-323 (1985), hereby incorporated by reference. The starting material is the plasmid (or other vector) comprising the nucleic acid encoding the hepatocyte secretory factor to be mutated. The codon(s) in the starting DNA to be mutated are identified. There should be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Biologically active fragment or variant of a hepatocyte secretory factor can be screened in assays known in the art to determine if such polypeptides are suitable for use in embodiments of the present invention. For example, one can screen such mutants and variants using the methods described in Examples (below), by substituting the candidate variants hepatocyte secretory factor for those described in Example 1 and determining if ischemic injury is reduced or prevented.

Alternatively, or additionally, the desired amino acid sequence encoding a polypeptide variant can be determined, and a nucleic acid sequence encoding such amino acid sequence variant can be generated synthetically. Conservative modifications in the amino acid sequences of hepatocyte secretory factors, or in the nucleic acids encoding such factors, may also be made by substituting an amino acid with an amino acid of the same class. Amino acid residues (e.g., natural and/or non-natural) are divided into classes based on common side-chain properties, for example:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

In some embodiments, the present invention employs variants of FGF21, such as those described in Pat. Pub. 20090305986 and U.S. Pat. No. 7,655,627 (both of which are herein incorporated by reference). In some embodiments, the present invention employs the proteins and peptides described in Pat. Pub. 20110008281-A1, or nucleic acids encoding such proteins and peptides. Examples of FGF21, RELMγ, and TFF3 polypeptide sequences, and nucleotide sequences encoding them, can be found in the sequence listing as SEQ ID NOs:1-6. Polypeptide sequences comprising, consisting of, and/or consisting essentially of SEQ ID NOs:1, 3, and/or 5, biologically active variants (e.g. >70% identity) and/or fragments thereof find use in embodiments described herein. Nucleotide sequences coding for polypeptides comprising, consisting of, and/or consisting essentially of SEQ ID NOs:1, 3, and/or 5, biologically active variants (e.g. >70% identity) and/or fragments thereof find use in embodiments described herein. Nucleotide sequences comprising, consisting of, and/or consisting essentially of SEQ ID NOs:2, 4, and/or 6, fragments thereof, and/or variants thereof find use in embodiments described herein.

In some embodiments, the present invention provides compositions and methods for prevention, treatment and/or alleviation of cerebral ischemic injury (e.g., cerebral infarction) resulting from stroke. In some embodiments, compositions of the present invention are provided as a pharmaceutical agent. When used for the purposes described herein, said pharmaceutical agent may be administered via any desired oral, parenateral, topical, intravenous, transmucosal, surgical, and/or inhalation routes. The pharmaceutical agent may be administered in the form of a composition which is formulated with a pharmaceutically acceptable carrier and optional excipients, flavors, adjuvants, etc. in accordance with good pharmaceutical practice.

In some embodiments of the present invention, compositions are administered to a patient alone or in combination with other therapies, pharmaceuticals, supplements, and/or a specified diet, or in pharmaceutical compositions where it is mixed with excipient(s) or other pharmaceutically acceptable carriers. In some embodiments of the present invention, the pharmaceutically acceptable carrier is pharmaceutically inert. In other embodiments of the present invention, compositions may be administered alone.

Depending on the goal of administration (e.g. type and severity of condition, duration of treatment, etc.), compositions may be formulated and administered systemically or locally (e.g., in the brain). Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

In some embodiments, compositions may be in the form of a solid, semi-solid or liquid dosage form: such as tablet, capsule, pill, powder, suppository, solution, elixir, syrup, suspension, cream, lozenge, paste and spray containing the first and second agents formulated appropriately to provide the desired time-release profile. As those skilled in the art would recognize, depending on the chosen route of administration, the composition form is selected.

In some embodiments, the pharmaceutical agent may be administered in single or multiple doses. The particular route of administration and the dosage regimen will be determined by one of skill, in keeping with the condition of the individual to be treated and said individual's response to the treatment. The present invention also provides pharmaceutical agents in a unit dosage form for administration to a subject, comprising pharmaceutical agents and one or more nontoxic pharmaceutically acceptable carriers, adjuvants or vehicles. The amount of the active agents (e.g. FGF21, RELMγ, TFF3, etc.) that may be combined with such materials to produce a single dosage form will vary depending upon various factors, as indicated above. A variety of materials can be used as carriers, adjuvants, and vehicles in the composition of the invention, as available in the pharmaceutical art.

In some embodiments, compositions of the present invention are co-administered with other therapeutics for treatment, prevention, or alleviation of cerebral ischemia or other neuronal damage or disorders. In some embodiments, active agents (e.g. FGF21, RELMγ, TFF3, etc.) are co-administered with any suitable agents (e.g., therapeutics, nutriceutical, pharmaceuticals, etc.), for treatment, prevention, symptom reduction, easing side effects of treatments, deducing drug interactions, etc.

EXAMPLES

The following Examples are presented in order to provide certain exemplary embodiments of the present invention and are not intended to limit the scope thereof.

Example 1

Neuroprotective Effect of Stroke-Induced Secretory Proteins

Cerebral Ischemia.

Cerebral ischemia was induced in the mouse by permanently ligating the right middle cerebral artery with 2-hr ligation of both common carotid arteries (Buchan A M, et al., 1992; herein incorporated by reference in its entirety). C57BL/6J mice were anesthetized by intraperitoneal injection of ketamine (100 mg/kg) and xylazine (10 mg/kg). A skin incision was made between the right eye and the external auditory canal. A 2 mm hole was drilled on the temporal bone near the zygomatic arch. The middle cerebral artery was permanently ligated with a silk suture thread at the first bifurcation above the zygomatic arch. Immediately following the ligation of the middle cerebral artery, both common carotid arteries were ligated for 2 hrs. Age- and gender-matched mice were used as controls with sham operation with identical procedures except that the middle cerebral and both carotid arteries were not ligated. The Institutional Animal Care and Use Committee approved all experimental procedures used in this investigation.

cDNA Microarray.

cDNA microarray analyses were conducted to test the gene expression profile in hepatocytes by using the Illumina whole-genome Mouse WG-6 v2 Expression Bead Chip with 45,200 transcripts. Hepatocytes were isolated from the liver of mice with cerebral ischemia and sham operation at day 1, 3, 5, and 10 by Percoll-mediated centrifugation. Total RNA was prepared from the isolated hepatocytes by using the TRIzol reagent kit of Invitrogen. cDNA and cRNA syntheses, cRNA chip hybridization, and data scanning were carried out according to the manufacturer's instruction. An average number of 41+/−8 spots were used for each gene. The target signal intensity values of all spots for each gene were averaged and used for data analyses. The acquisition and initial quantification of array images were achieved using the Illumina Genome Studio Gene Expression Module v1.0 software. The target signal intensity was normalized with reference to the median intensity value. Criteria for selecting differentially expressed genes in the hepatocytes of mice with cerebral ischemia were set at a 3-fold change compared to the sham control at a given time and a detection p-value at p<0.05 based on the comparison of the target signal with the negative control. Upregulated genes encoding secreted proteins were further tested and analyzed for selecting neuroprotective factors.

Identification of Secreted Factors Effective for Neuroprotection.

To identify factors effective for neuroprotection from the population of upregulated genes encoding secreted proteins, the recombinant form of each upregulated secreted factor was administered to mice with cerebral ischemia and tested changes in the volume fraction of cerebral infarcts. A selected recombinant protein was injected IV at a dose of 50 ng/gm twice per day starting immediately following the induction of cerebral ischemia. Mouse serum albumin at the same dose was used as a control. The volume fraction of cerebral infarcts was tested by the TTC assay at 24 hrs post cerebral ischemia. A protein was considered effective for neuroprotection when its administration resulted in a significant reduction in the volume fraction of cerebral infarcts compared to the albumin control.

Measurement and Analysis of Cerebral Infarcts.

The degree of cerebral injury was evaluated based on the volume fraction of cerebral infarcts with reference to the total volume of the cerebrum. The 2,3,5-triphenyltetrazolium chloride (TTC) assay was used for staining and measuring the intact and infarcted brain at 24 hrs of cerebral ischemia as described (Liu and Wu, 2010a). A fresh mouse brain was collected, frozen rapidly at −66° C. for 5 min on a pre-cooled rubber pad, and cut into 1-mm thick slices using a blade with a 1-mm spacer. The brain slices were incubated in 1% TTC/PBS at 37° C. for 30 min, fixed in 4% formaldehyde/PBS for 15 min, and photographed with the aid of a surgical microscope.

TTC stains intact brain red and infarcts white. As there exists a wide transition zone with a gradient of red intensity from the red to the white region, it is often difficult to accurately and reproducibly identify the boundary of the infarct, resulting in intra- and inter-observer measurement errors. To resolve this problem, a statistical model was established to define the cerebral infarct boundary in TTC-stained specimens based on RGB-formatted images. In this model, the red, green, and blue color intensities were measured from image regions randomly selected from the intact brain of each tested specimen. A TTC index was calculated for each image region to represent the red intensity by using the following equation:

TTC index=Red intensity/(Red intensity+Green intensity+Blue intensity).

An equal intensity for all three colors, except for zero, gives a TTC index 1/3, representing the white color. A definite red intensity with a zero green and blue intensity gives a TTC index 1, representing a pure red color. The TTC index for all measured image regions from the intact brain of each specimen was analyzed to test the statistical distribution. The TTC index follows a normal distribution pattern in TTC-stained brain specimens. The mean and standard deviation of the TTC index were calculated for each specimen. A TTC boundary index for identifying the red-white or intact-infarcted brain boundary was defined based on the statistical principle of population identification:

Boundary index=Mean of TTC index−1.96×standard deviation.

This index represents the boundary of a cerebral infarct. An image region with a TTC index>the boundary index was considered a portion of the intact brain, whereas an image region with a TTC index<the boundary index was considered a portion of the infarct. The total area of the red or white regions represents the area of the intact or infarcted brain, respectively. The volume fraction of the intact and infarcted brain was calculated with reference to the total volume of the cerebrum.

Measurement and Analysis of Mouse Forelimb Gripping Strength.

Cerebral ischemia induces impairment of the motor function of skeletal muscles. In this investigation, the forelimb gripping force was measured and analyzed to assess the degree and progression of cerebral injury in response to ischemic insults with and without a treatment with a secreted factor. A torque device was developed for testing the mouse forelimb gripping force (SEE FIG. 1). During the test, a mouse was tail-lifted, one of the mouse forelimbs was wrapped with a piece of a Scotch tape to prevent the limb from gripping, and the other forelimb was allowed to grip a small ring (1 cm) attached to the arm of a torque sensor (arm length 5 cm). The mouse was tail-pulled slowly in the direction perpendicular to the arm of the torque sensor until the mouse gave up gripping the arm ring. The mouse forelimb gripping force was recorded continuously during the test via a data acquisition system. The recorded data were converted to gripping forces based on calibrations derived by using 10, 20, and 30 gm weights.

Upregulation of Hepatocyte Genes Encoding Secreted Factors in Cerebral Ischemia.

Figure 2:
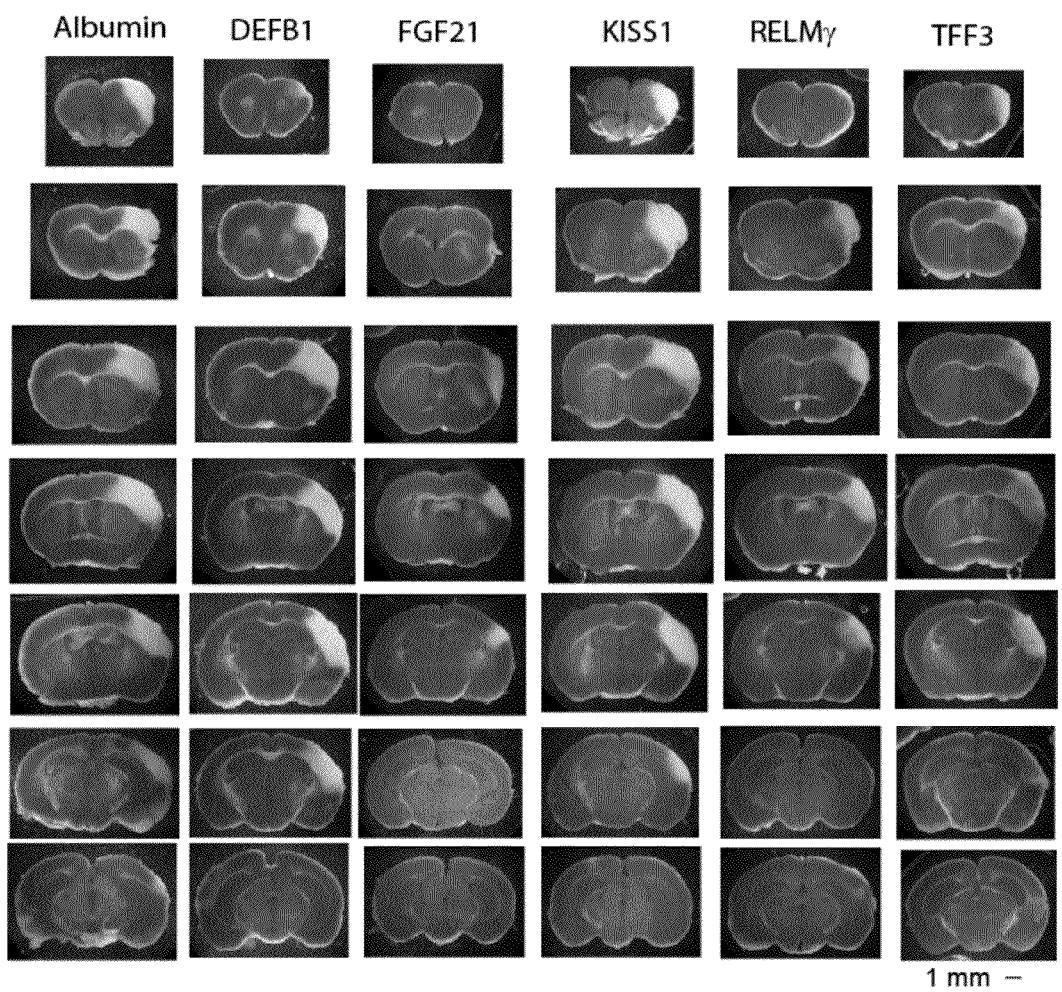
FIG. 2 shows images of slices of mouse cerebrum for identification of secreted factors effective for neuroprotection in cerebral ischemia. Each column represents specimen slices from different locations of the mouse cerebrum with administration of albumin or a secreted factor. Specimens were stained with 1% TTC/PBS. Darker regions represents intact brain, and the white represents brain infarcts. The scale is for all panels.

Cerebral ischemia induced upregulation of hepatocyte genes encoding secreted proteins, including defensin beta 1 (DEFB1), fibroblast growth factor 21 (FGF21), kisspeptin (KISS1), resistin-like molecule γ (RELMγ), serum amyloid A (SAA) 1, SAA2, trefoil factor 3 (TFF3). The maximal level of mRNA transcription was found at day 1 for the DEFB1, FGF21, KISS1, and RELMγ genes, and at day 5 for the SAA1 and SAA2 genes post cerebral ischemia (SEE FIG. 2). The TFF3 gene exhibited two episodes of transcription upregulation at day 1 and 5. The maximal relative level of mRNA transcription was 3.2, 3.3, 4.4, and 3.1 times of the sham control level for the DEFB1, KISS1, RELMγ, and TFF3 genes, respectively, 9.6 times for the FGF21 gene, and 25.4 and 15.4 times for the SAA1 and SAA2 genes, respectively. In this investigation, we tested the neuroprotective effect of DEFB1, FGF21, KISS1, RELMγ, and TFF3. SAA1 and SAA2 were not tested, because these factors are known to induce amyloidosis, resulting in impairment of cell and tissue functions (Westermark and Westermark, 2009; herein incorporated by reference in its entirety).

Effect of Secreted Factor Administration on Cerebral Infarction.

Figure 3:
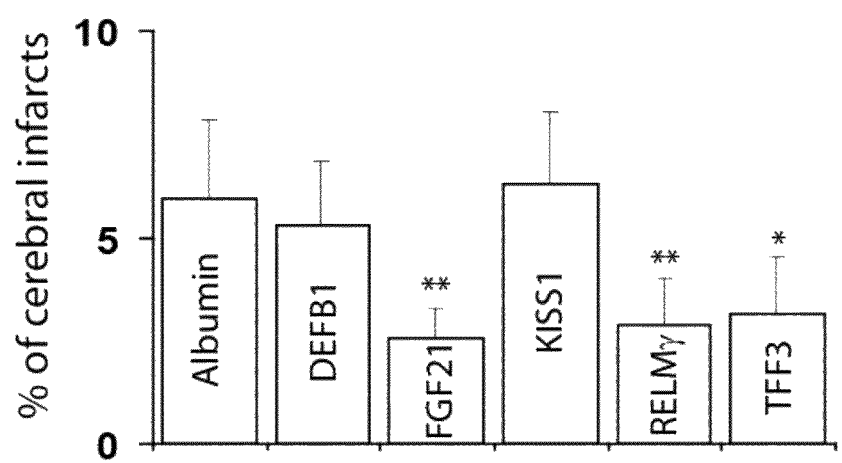
FIG. 3 shows a graphic representation of the neuroprotective effect of secreted factors FGF21, RELMγ, and TFF3 at 24 hrs of cerebral ischemia. The % represents volume fraction of cerebral infarcts with reference to the total volume of the cerebrum.
Figure 4:
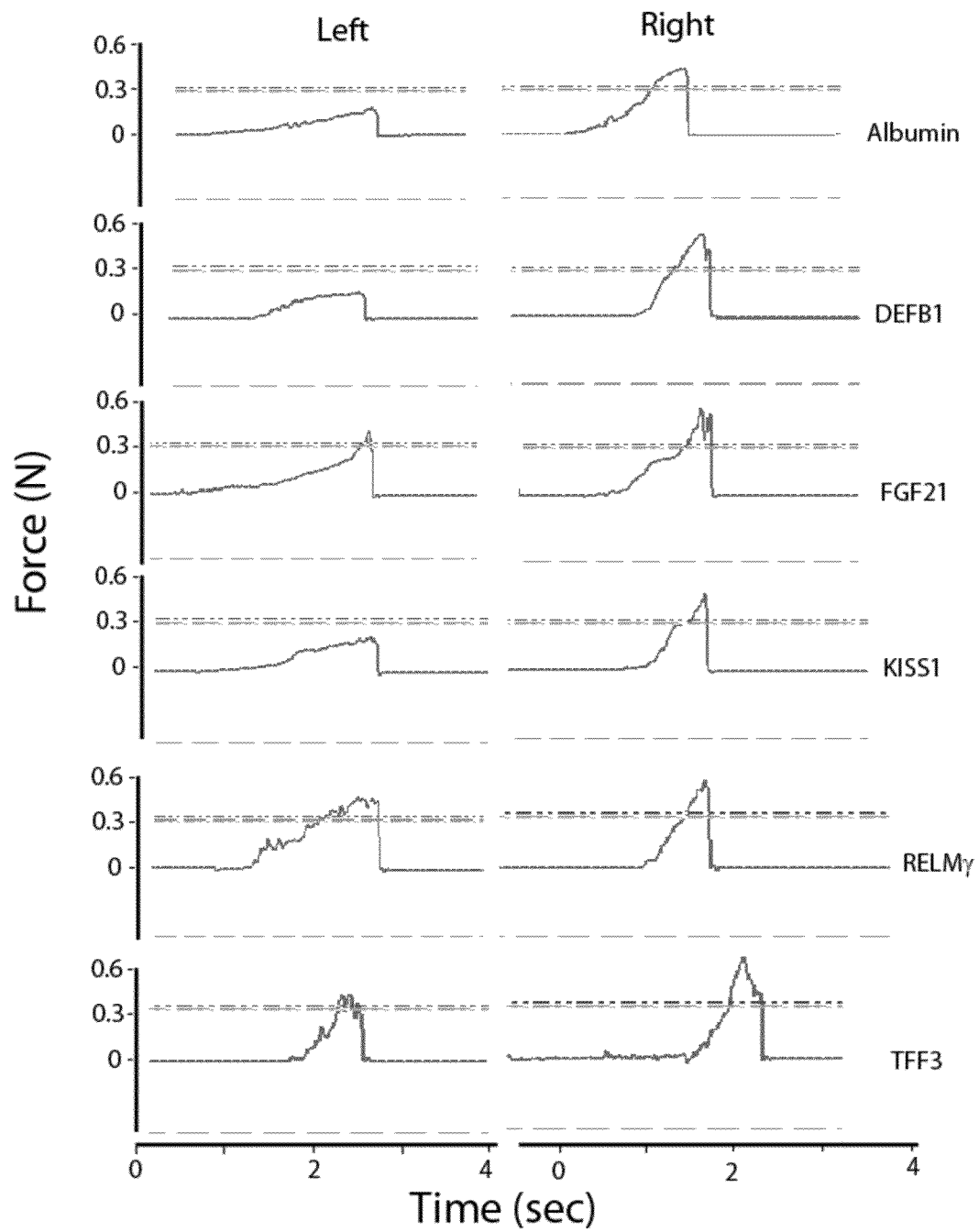
FIG. 4 shows a plot of gripping forces of the left and right forelimbs of mice with right hemispheric cerebral ischemia with administration of albumin or a secreted factor.

To test the neuroprotective effect of DEFB1, FGF21, KISS1, RELMγ, and TFF3, the mouse recombinant form of each protein was administered to mice with cerebral ischemia at the dose of 50 ng/gm twice per day starting immediately post cerebral ischemia, and tested the effect of the administration on the volume fraction of cerebral infarcts at 24 hrs by the TTC assay, while albumin was used as a control agent. Administration of FGF21, RELMγ, or TFF3 resulted in a significant reduction in the volume fraction of cerebral infarcts at 24 hrs, whereas administration of DEFB1 or KISS1 did not induce a significant change (SEE FIGS. 3 and 4). Thus, FGF21, RELMγ, and TFF3 were identified as potential neuroprotective factors in this investigation.

Effect of Secreted Factor Administration on the Gripping Strength of the Impaired Forelimb.

Figure 5:
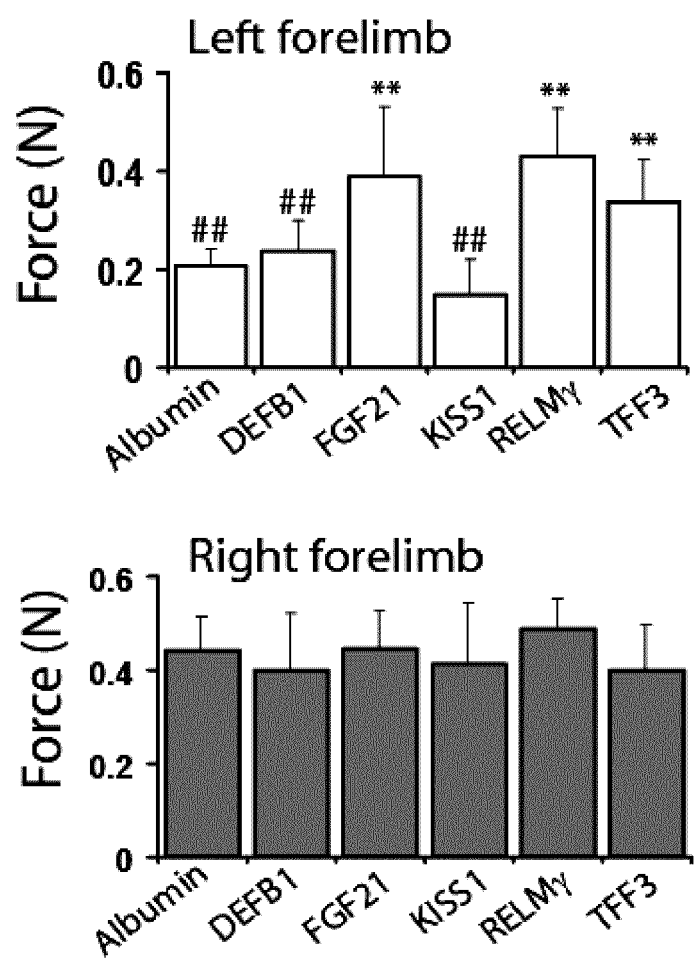
FIG. 5 shows histograms of measured gripping forces of the left and right forelimbs of mice with right hemispheric cerebral ischemia with administration of albumin or a secreted factor.

Cerebral ischemia induced a significant reduction in the gripping strength of the opposite forelimb. Experiments were conducted during development of embodiments of the present invention to determine whether administration of DEFB1, FGF21, KISS1, RELMγ, or TFF3 improved the gripping strength of the impaired forelimb in mice with cerebral ischemia. While administration of DEFB1 or KISS1 at the dose of 50 ng/gm twice per day did not influence the forelimb gripping strength at 24 hrs of cerebral ischemia, administration of FGF21, RELMγ, or TFF3 significantly improved the gripping strength of the impaired forelimb (SEE FIGS. 5 and 6). These observations were consistent with the results presented in the section above, suggesting that FGF21, RELMγ, and TFF3 exerted a protective effect on the motor control function of the central nerve system in cerebral ischemia.

The liver is a unique organ that possesses a high capacity of protection and regeneration in mechanical and chemical injuries. Live cells, including hepatocytes, biliary epithelial cells, endothelial cells, Kupffer cells, an Ito cells, are capable of initiating rapid proliferation during liver regeneration (Alison et al., 1998; Fausto and Campbell, 2003; Forbes et al., 2002; Michalopoulos and DeFrances, 1997; Taub, 2004; herein incorporated by reference in their entireties). Observations from this investigation suggest that the liver cells are not only responsible for liver protection and regeneration, but also contribute to protection of ischemic brain tissues. These observations provide a basis for investigations of liver responses to brain injuries.

All publications and patents mentioned in the present application and/or listed below are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

Alison M, Golding M, Lalani El-N & Sarraf C. Philos Trans R Soc Lond B Biol Sci 353, 877-894, 1998.
Buchan A M, et al., Stroke 23:273-279, 1992
Chumakov A M, Kubota T, Walter S, Koeffler H P (2004). Oncogene 23: 3414-3425
Dostálová I, Haluziková D, and Haluzik M. Physiol Res 58, 1-7, 2009.
Fausto N, and Campbell J S (2003). Mech Dev 120, 117-130.
Forbes S, Vig P, Poulsom R, Thomas H, and Alison M. J. Pathol. 197, 510-518, 2002.
Gerstmayer B, Kusters D, Gebel S et at (2003). Genomics 81:588-595
Ibrahimi O A, Zhang F, Hrstka S C, Mohammadi M, Linhardt R T. Biochemistry 43: 4724-4730, 2004.
Itoh N, Ornitz D M. Trends Genet 20: 563-569, 2004.
Kharitonenkov A, Shiyanova T L, Koester A, Ford A M, Micanovic R, Galbreath E J, Sandusky G E, Hammond L J, Moyers J S, Owens R A, Gromada J, Brozinick J T, Hawkins E D, Wroblewski V J, Li D S, Mehrbod F, Jaskunas S R & Shanafelt A B (2005). J Clin Invest 115, 1627-1635.
Liu S Q, and Wu Y H. Frontiers in Bioscience (Elite Ed) 2:711-24, 2010a.
Liu S Q. and Wu Y H. Current Topics in Biochemical Research, 2010b, in press.
Shu Q. Liu, Yupeng Ren, Brandon Tefft, Yi-Ning Wu, Charley Liu, Yan Chun Li, Li-Qun Zhang, Barry Walker, Harry R. Phillips, Yu H. Wu. 2010, submitted.
Michalopoulos G K & DeFrances M C (1997). Science 276, 60-66.
Mohammadi M, Olsen S K, Goetz R. Curr Opin Struct Biol 15: 506-516, 2005.
Nair M G, Guild K J, and Artis D. J. Immunol. 2006; 177; 1393-1399
Nishimura T, Nakatake Y, Konishi M, and Itoh N. Biochim Biophys Acta 1492: 203-206, 2000.
Ryde'n M. Cell. Mol. Life Sci. 66:2067-2073, 2009.
Sands B E, and Podolsky D K. Annu Rev. Physiol. 58:253-273, 1996.
Schinke T, Haberland M, Jamshidi A et at (2004). Biochem Biophys Res Commun 314:356-362
Shojima N., Ogihara T. Inukai K., Fujishiro M., Sakoda H., Kushiyama A., Katagiri H., M. Anai M., Ono H., Fukushima Y., Horike N., Viana A. Y. I., Uchijima Y., Kurihara H., Asano T. Diabetologia 48: 984-992, 2005.
Steppan C M, Bailey S T, Bhat S, Brown E J, Banerjee R R, Wright C M, Patel H R, Ahima R S, Lazar M A. Nature. 2001 Jan. 18; 409(6818):307-12.
Taub R (2004). Nat Rev Mol Cell Biol 5, 836-847.
Westermark G T, Per Westermark. FEBS Letters 583: 2685-2690, 2009.
Wong W M, Poulsom R, Wright N A. Gut 44:890-895, 1999.
Zhang X, Ibrahimi O A, Olsen S K, Umemori H, Mohammadi M, Ornitz D M. J Biol Chem 281: 15694-15700, 2006.

I claim:

1. A method of treating a subject experiencing cerebral ischemia comprising: administering a composition to said subject, wherein said composition comprises at least one isolated hepatocyte secretory factor, wherein said at least one isolated hepatocyte secretory factor is TFF3 (Trefoil Factor 3).

2. The method of claim 1, wherein administration of said composition reduces ischemic injury in said subject.

3. The method of claim 1, wherein administration of said composition exerts a neuroprotective effect.

4. The method of claim 1, wherein administration of said composition results in reduction in cerebral infarction.

5. The method of claim 1, wherein said subject is a mammal.

6. The method of claim 5, wherein said subject is a human.

* * * * *

SEQUENCE LISTING

<160> NUMBER OF SEQ ID NOS: 6

<210> SEQ ID NO 1
<211> LENGTH: 208
<212> TYPE: PRT
<213> ORGANISM: Homo sapiens

<400> SEQUENCE: 1

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro Asp
            20                  25                  30

Ser Ser Pro Leu Leu Gln Phe Gly Gly Gln Val Arg Gln Arg Tyr Leu
        35                  40                  45

Tyr Thr Asp Asp Ala Gln Gln Thr Glu Ala His Leu Glu Ile Arg Glu
    50                  55                  60

Asp Gly Thr Val Gly Gly Ala Ala Asp Gln Ser Pro Glu Ser Leu Leu
65                  70                  75                  80

Gln Leu Lys Ala Leu Lys Pro Gly Val Ile Gln Ile Leu Gly Val Lys
                85                  90                  95

Thr Ser Arg Phe Leu Cys Gln Arg Pro Asp Gly Ala Leu Tyr Gly Ser
            100                 105                 110

Leu His Phe Asp Pro Glu Ala Cys Ser Phe Arg Glu Leu Leu Leu Glu
        115                 120                 125

Asp Gly Tyr Asn Val Tyr Gln Ser Glu Ala His Gly Leu Pro Leu His
    130                 135                 140

Leu Pro Gly Asn Lys Ser Pro His Arg Asp Pro Ala Pro Arg Gly Pro
145                 150                 155                 160

Ala Arg Phe Leu Pro Leu Pro Gly Leu Pro Pro Ala Leu Pro Glu Pro
                165                 170                 175

Pro Gly Ile Leu Ala Pro Gln Pro Pro Asp Val Gly Ser Ser Asp Pro
            180                 185                 190

Leu Ser Met Val Gly Pro Ser Gln Gly Arg Ser Pro Ser Tyr Ala Ser
        195                 200                 205

<210> SEQ ID NO 2
<211> LENGTH: 940
<212> TYPE: DNA
<213> ORGANISM: Homo sapiens

<400> SEQUENCE: 2
ctgtcagctg aggatccagc cgaaagagga gccaggcact caggccacct gagtctactc      60
acctggacaa ctggaatctg gcaccaattc taaaccactc agcttctccg agctcacacc     120
ccggagatca cctgaggacc cgagccattg atgactcgg acgagaccgg gttcgagcac      180
tcaggactgt gggtttctgt gctggctggt cttctgctgg gagcctgcca ggcacacccc     240
atccctgact ccagtcctct cctgcaattc gggggccaag tccggcagcg gtacctctac     300
acagatgatg cccagcagac agaagcccac ctggagatca ggaggatgg gacggtgggg      360 ggcgctgctg accagagccc cgaaagtctc ctgcagctga agccttgaa gccgggagtt      420 attcaaatct tgggagtcaa gacatccagg ttcctgtgcc agcggccaga tggggccctg     480
tatggatcgc tccactttga ccctgaggcc tgcagcttcc gggagctgct tcttgaggac     540
ggatacaatg tttaccagtc cgaagcccac ggcctcccgc tgcacctgcc agggaacaag     600
tccccacacc gggaccctgc accccgagga ccagctcgct tcctgccact accaggcctg     660

```
cccccccgcac tcccggagcc acccggaatc ctggccccccc agccccccga tgtgggctcc    720
tcggaccctc tgagcatggt gggaccttcc cagggccgaa gccccagcta cgcttcctga    780
agccagaggc tgtttactat gacatctcct ctttatttat taggttattt atcttattta    840 ttttttatt tttcttactt gagataataa agagttccag aggagaaaaa aaaaaaaaaa    900
aaaaaaaaaa aaaaaaaaaa aaaaaaaaaa aaaaaaaaaa    940
```

```
<210> SEQ ID NO 3
<211> LENGTH: 117
<212> TYPE: PRT
<213> ORGANISM: Mus musculus

<400> SEQUENCE: 3

Met Leu Thr Phe Asn Lys Met Lys Thr Thr Thr Cys Ser Leu Leu Ile
1               5                   10                  15

Cys Ile Ser Leu Leu Gln Leu Met Val Pro Val Asn Thr Glu Gly Thr
            20                  25                  30

Leu Glu Ser Ile Val Glu Lys Val Lys Glu Leu Leu Ala Asn Arg
        35                  40                  45

Asp Asp Cys Pro Ser Thr Val Thr Lys Thr Phe Ser Cys Thr Ser Ile
    50                  55                  60

Thr Ala Ser Gly Arg Leu Ala Ser Cys Pro Ser Gly Met Thr Val Thr
65                  70                  75                  80

Gly Cys Ala Cys Gly Tyr Gly Cys Gly Ser Trp Asp Ile Arg Asp Gly
                85                  90                  95

Asn Thr Cys His Cys Gln Cys Ser Thr Met Asp Trp Ala Thr Ala Arg
            100                 105                 110

Cys Cys Gln Leu Ala
        115
```

```
<210> SEQ ID NO 4
<211> LENGTH: 610
<212> TYPE: DNA
<213> ORGANISM: Mus musculus

<400> SEQUENCE: 4
gcttgtatat agtaagggta cacaggtcag taatcccacg gtgtattaaa gcatctcatc    60
tggccaggtc ctggaacctt tcctgagatt ctgcctagg atgctgactt tcaacaagat    120
gaagactaca acttgttccc ttctcatctg catctccctt ctccagctga tggtcccagt    180
gaatactgag gggaccttag aatctattgt ggagaaaaag gtcaaggaac ttcttgccaa    240
tcgagatgac tgtccctcca ctgtaacaaa gactttctcc tgtactagta tcacggcttc    300
aggcagactg gcctcctgtc cttctggaat gactgtcact ggttgtgctt gtggctatgg    360
ctgtggatct tgggatatcc gggatggaaa tacttgccac tgtcagtgct caacaatgga    420
ctgggccacc gcccgttgct gccaactggc ctaagaatga ggaagctgag aacctagctt    480
tgaaatgaag actataacaa aagcacaatc ccaacttgga aacctggctc atatcccatt    540
gatgaattca tattgtccat tagccctgct tcttgaaaaa ataaagaca aatttgcacg    600 tgtctgtaaa    610
```

```
<210> SEQ ID NO 5
<211> LENGTH: 73
<212> TYPE: PRT
<213> ORGANISM: Homo sapiens

<400> SEQUENCE: 5
```

```
Met Leu Gly Leu Val Leu Ala Leu Leu Ser Ser Ser Ala Glu Glu
1               5                   10                  15

Tyr Val Gly Leu Ser Ala Asn Gln Cys Ala Val Pro Ala Lys Asp Arg
            20                  25                  30

Val Asp Cys Gly Tyr Pro His Val Thr Pro Lys Glu Cys Asn Asn Arg
        35                  40                  45

Gly Cys Cys Phe Asp Ser Arg Ile Pro Gly Val Pro Trp Cys Phe Lys
    50                  55                  60

Pro Leu Gln Glu Ala Glu Cys Thr Phe
65                  70

<210> SEQ ID NO 6
<211> LENGTH: 222
<212> TYPE: DNA
<213> ORGANISM: Homo sapiens

<400> SEQUENCE: 6
atgctggggc tggtcctggc cttgctgtcc tccagctctg ctgaggagta cgtgggcctg      60
tctgcaaacc agtgtgccgt gccagccaag gacagggtgg actgcggcta cccccatgtc     120 accccccaagg agtgcaacaa ccggggctgc tgctttgact ccaggatccc tggagtgcct    180
tggtgtttca gcccctgca ggaagcagaa tgcaccttct ga                        222
```